(12) United States Patent
Luke

(10) Patent No.: US 6,542,230 B1
(45) Date of Patent: Apr. 1, 2003

(54) APPARATUS FOR PERFORMING OPERATIONS ON A WORKPIECE AT AN INACCESSIBLE LOCATION

(75) Inventor: Barry Edward Luke, Canvey Island (GB)

(73) Assignee: Keymed (Medical & Industrial) Ltd., Southend-on-Sea (GB)

( * ) Notice: Subject to any disclaimer, the term of this patent is extended or adjusted under 35 U.S.C. 154(b) by 0 days.

(21) Appl. No.: 09/744,753

(22) PCT Filed: Jul. 16, 1999

(86) PCT No.: PCT/GB99/02299

§ 371 (c)(1),
(2), (4) Date: Jan. 29, 2001

(87) PCT Pub. No.: WO00/06336

PCT Pub. Date: Feb. 10, 2000

(30) Foreign Application Priority Data

Jul. 28, 1998 (GB) .............................................. 9816421

(51) Int. Cl.⁷ .............................................. G01N 21/00
(52) U.S. Cl. .................................................. 356/241.1
(58) Field of Search .......................... 356/241.1–241.6, 356/237.1, 3.1–3.12

(56) References Cited

U.S. PATENT DOCUMENTS

| | | | |
|---|---|---|---|
| 5,155,941 A | 10/1992 | Takahashi et al. ........ 51/165.72 |
| 5,222,174 A | 6/1993 | Miles .......................... 385/118 |
| 5,373,317 A | 12/1994 | Salvati et al. .................. 348/65 |
| 5,540,677 A | 7/1996 | Sinofsky ......................... 606/8 |
| 5,573,531 A | 11/1996 | Gregory ...................... 606/14 |
| 6,011,617 A | * 1/2000 | Naudet ..................... 356/237.1 |

FOREIGN PATENT DOCUMENTS

| | | |
|---|---|---|
| DE | 42 09 926 | 9/1993 |
| EP | 0 587 506 | 3/1994 |
| GB | 2 222 737 | 3/1990 |
| GB | 2 280 514 | 2/1995 |

* cited by examiner

Primary Examiner—Michael P. Stafira
(74) Attorney, Agent, or Firm—Smith, Gambrell & Russell

(57) ABSTRACT

An apparatus and method for performing an operation on a workpiece at an inaccessible location are described. The apparatus includes a tube with proximal and distal ends, the distal end being insertable in use into an inaccessible location. A head is flexibly coupled to the distal end of the tube and can be moved relative to the tube by control means. Laser energy can be transmitted through the tube and out of the head. The apparatus includes viewing means for gathering and displaying an image of the workpiece and tracking means operable to identify and record the position of one or more selected points of the workpiece. A processor is provided to actuate the control means so as to move the head to direct the laser energy to the selected point or points of a workpiece and to control the laser so as to perform the desired operation on the workpiece.

35 Claims, 8 Drawing Sheets

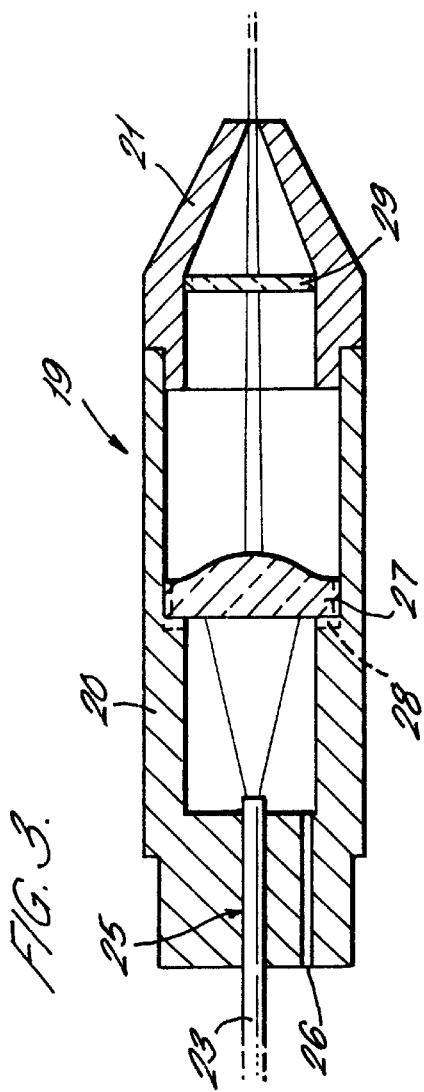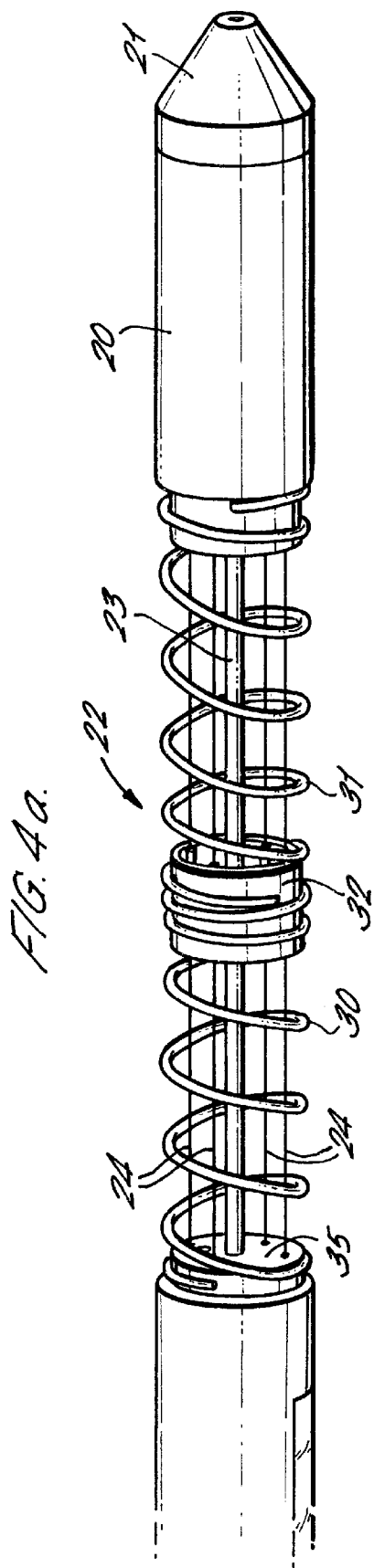
FIG. 3.
FIG. 4a.

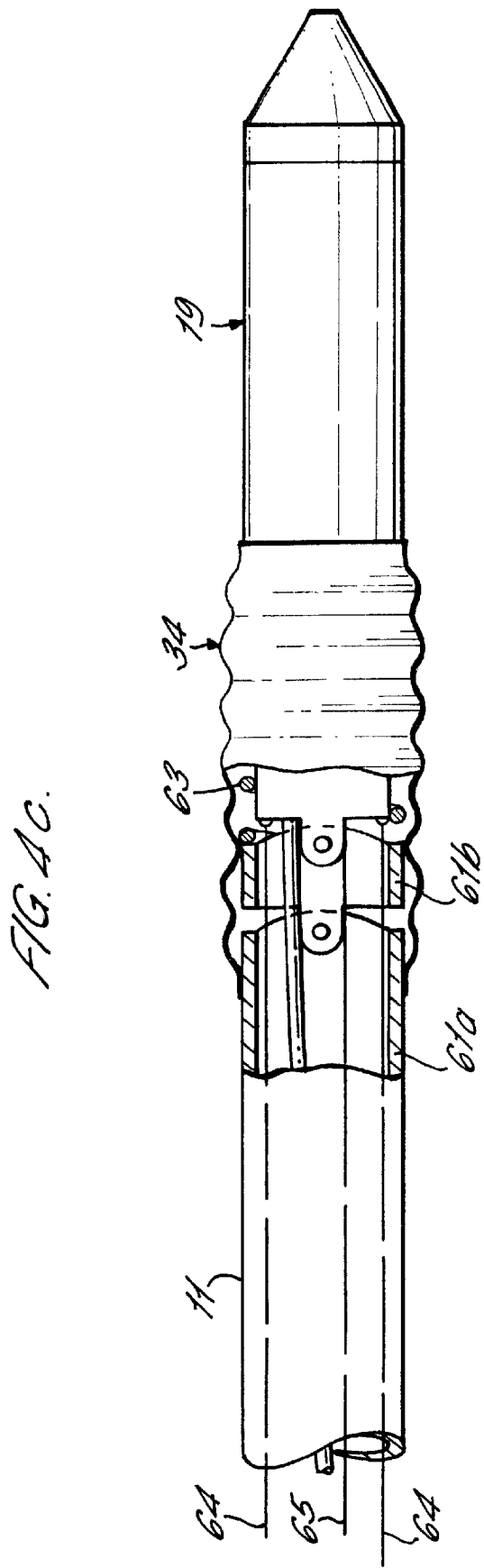

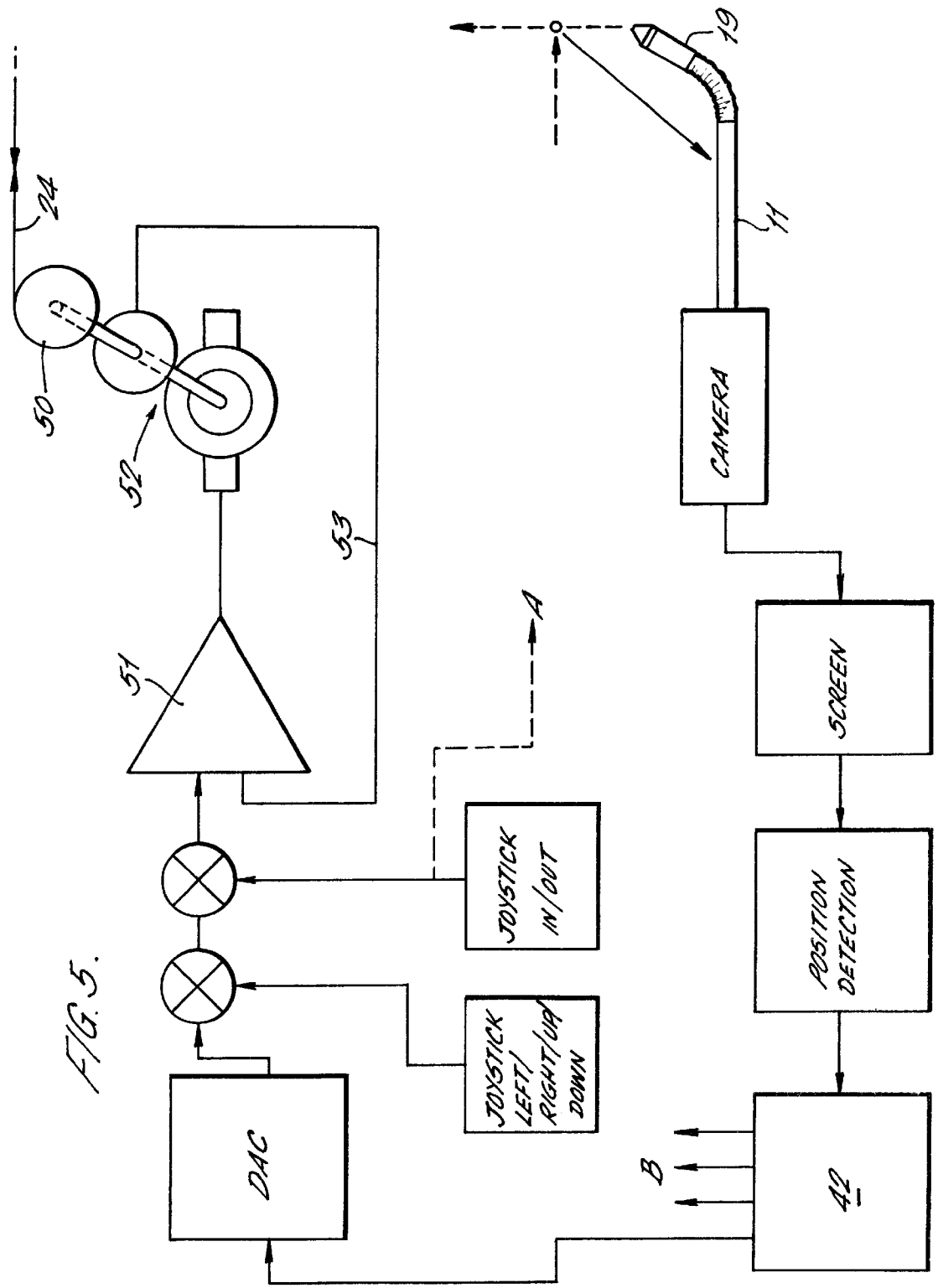

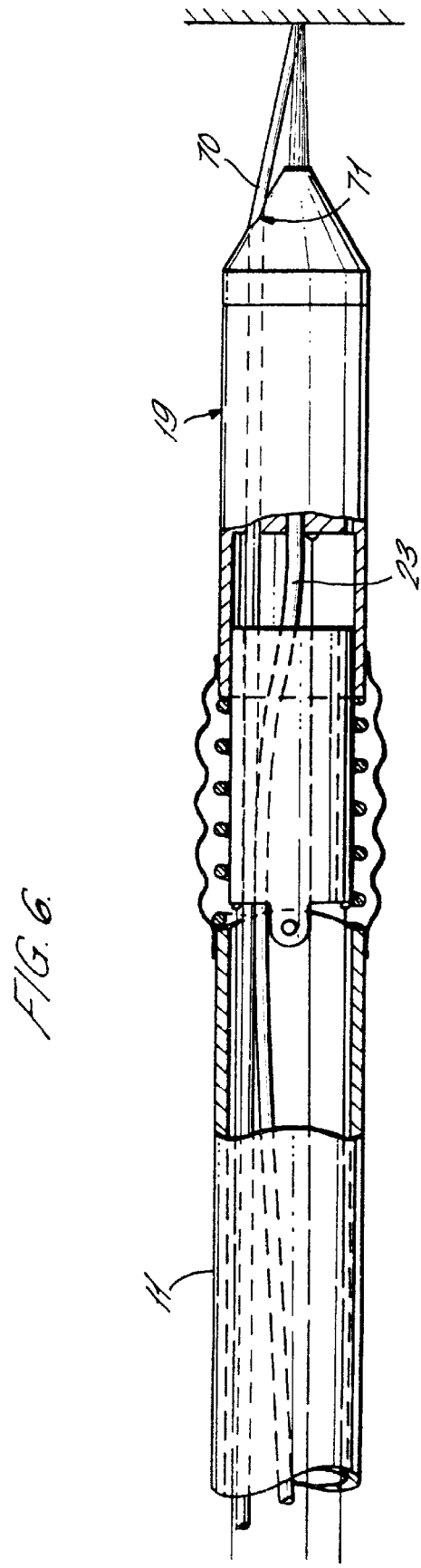

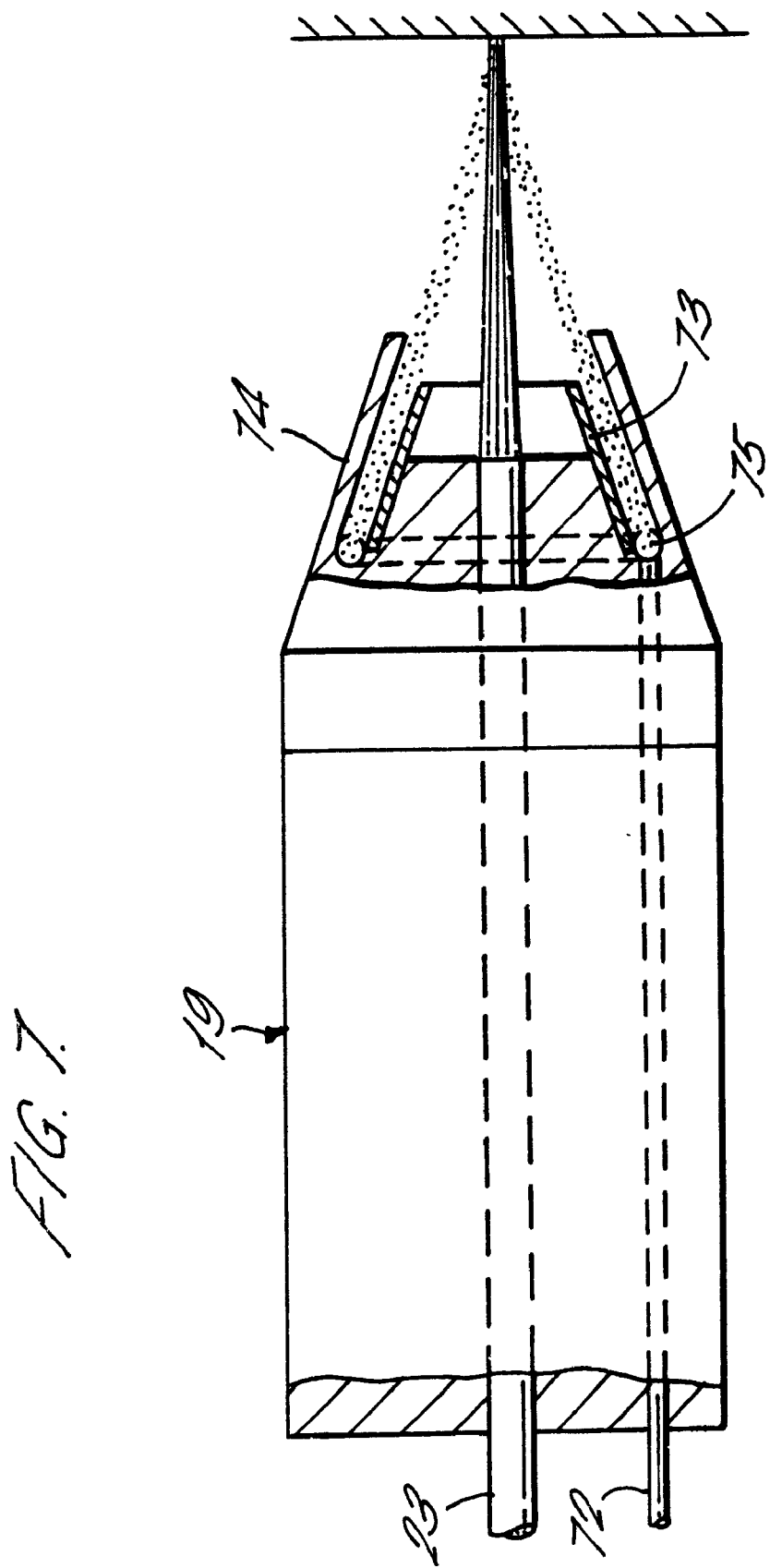

APPARATUS FOR PERFORMING OPERATIONS ON A WORKPIECE AT AN INACCESSIBLE LOCATION

BACKGROUND OF THE INVENTION

The present invention relates to apparatus for viewing a workpiece at an inaccessible location and performing operations, in particular by means of laser energy, on the workpiece.

It is well-known to employ optical scopes such as borescopes and endoscopes in order to view features in remote and/or inaccessible locations, such as the internal components of a machine. In particular, borescopes are frequently used to internally inspect gas turbine engines. If cracks or other defects are noted in components such as turbine blades, the engine is usually stripped down to provide access to the blade for its repair or replacement.

Since strip down of an engine is a time consuming and therefore expensive process, some systems have been developed which allow a certain amount of remedial work on a defect in a turbine blade to be carried out in situ. For example, U.S. Pat. No. 5,155,941 discloses an optical scope which includes a treatment member in the form of a miniature grinding tool which can be applied to a turbine blade. One problem with this type of system is that the remedial tool must contact the workpiece and since the tool is spinning, it creates a reaction torque.

SUMMARY OF THE INVENTION

The present invention provides apparatus for performing an operation on a workpiece at an inaccessible location, comprising a tube having a proximal end and a distal end, the distal end being insertable in use into an inaccessible location; a head flexibly coupled to the distal end of the tube; control means operable to adjust the position of the head with respect to the tube; means to transmit laser energy through the tube to the head and out of the head; viewing means for gathering and displaying an image of the workpiece; tracking means operable to identify and record the position of one or more selected points on the workpiece; a processor operable to actuate the control means to move the head so as to direct laser energy to the selected point or, sequentially, to each of the selected points on the workpiece and to control the laser transmission means so as to perform the desired operation.

The apparatus of the invention therefore allows remedial work to be carried out in situ without physically contacting the workpiece.

In a first embodiment, the tracking means comprises means to transmit a beam of visible light through the tube and out of the head, manual actuation means operable to move the head so as to direct the light beam to strike one or, sequentially, more than one desired point on the workpiece and wherein the processor is operable to record data representative of the position of the or each point.

The manual actuation means may comprise a joystick.

The laser transmission means may be adapted to selectively supply a lower power visible laser beam and a higher power laser beam for performing operations on the workpiece.

In another embodiment, the tracking means may comprise means to record the position of one or more selected points on the displayed image of the workpiece and wherein the processor is operable to relate the position of the or each point to the position of the head so as to actuate the control means to move the head to direct laser energy to the point, or, sequentially, to each point.

Conveniently, the viewing means comprises an optical scope integral with the tube.

Alternatively, the viewing means may comprise an optical scope removably located in the tube.

Preferably, the viewing means further comprises one of a camera and an image-to-video conversion device, and a display.

The viewing means may adapted for viewing laterally of the distal end of the tube.

Preferably, the control means and flexible coupling are selectively operable to move the head relative to the tube in three dimensions.

In one embodiment, the flexible coupling comprises spring means extending between the distal end of the tube and the head.

In another embodiment, the flexible coupling comprises at least one cylinder mounted between the tube and the head for pivotal movement relative to the tube, a sleeve attached to the head and axially moveable relative to the cylinder and spring means urging the head axially away from the tube.

The control means may comprise a plurality of pull elements secured to the head, and to the cylinder if present, and extending through the tube and means to retract and extend the pull elements.

Conveniently, the pull elements comprise wires.

The proximal end of each wire may be wound around a rotatable cylinder.

The flexible coupling may be encased in a flexible sleeve attached to the tube and to the head.

This flexible sleeve may be attached to the head and to the tube in a gas tight manner.

The means to transmit laser energy preferably comprises an optical fibre.

In one embodiment, the optical fibre terminates in the head and the head further includes means to focus a laser beam emitted from the optical fibre.

The focusing means may comprise a train of lenses and/or include an aspheric lens.

A protective screen is preferably provided in the head, distally of the focusing means.

Alternatively, the optical fibre may extends out of the head.

In this case, the distal end of the optical fibre may be shaped so as to emit a focussed laser beam from the optical fibre.

Alternatively, the distal end of the optical fibre may be shaped so as to emit a divergent laser beam from the optical fibre.

A laser filter may be provided to protect the viewing means from laser energy.

The viewing means may further include a filter to pass infra-red radiation only for display.

The tube and head are preferably, adapted to allow gas flow therethrough.

In this case, the apparatus may further comprise a gas supply for supplying pressurised gas or a mixture of gases to the tube and head.

Preferably, the gas is, or the mixture of gases includes, an inert gas.

The gas, or the mixture of gases, may include oxygen.

The apparatus may further comprise means to feed filler material through the tube and to dispense the filler material from the head.

In a another aspect the present invention also provides a method performing an operation on a workpiece at an inaccessible location utilizing the aforementioned apparatus, comprising the steps of positioning the tube with its distal end in the vicinity of the workpiece; gathering an image of the workpiece with the viewing means and displaying the image; identifying and recording the position of one or more selected points on the workpiece; and operating the processor to move the head and to supply laser energy through the tube so as to direct the laser energy to the point or, sequentially, to each point so as to perform a desired operation.

The identifying and recording step may comprise transmitting a beam of visible light through the tube and out of the head; adjusting the position of the head with manual actuation means so as to direct the light beam to strike a selected point on the workpiece; recording the position of the point and, optionally, repeating the process on one or more further points.

Alternatively, the identifying and recording step may comprise viewing an image of the workpiece on a display; marking the position of a point on the workpiece on the display; recording the position of the point and, optionally, repeating the process on one or more further points.

The invention will now be described in detail, by way of example only, with reference to the accompanying drawings in which:

BRIEF DESCRIPTION OF THE DRAWINGS

FIG. 3 is an enlarged cross section of the working head of the insertion tube in FIG. 2;

FIG. 4a is an enlarged perspective view of the flexible coupling in FIG. 2;

FIG. 4c is a side view, partly in cross-section, of another alternative flexible coupling;

FIG. 5 is a schematic diagram of part of the control system for the flexible coupling.

FIG. 6 is a side view of an insertion tube adapted for dispensing welding filler rod; and FIG. 7 is a side view of a head for dispensing welding filler powder.

DETAILED DESCRIPTION OF THE INVENTION AND PREFERRED EMBODIMENTS

Figure 1:
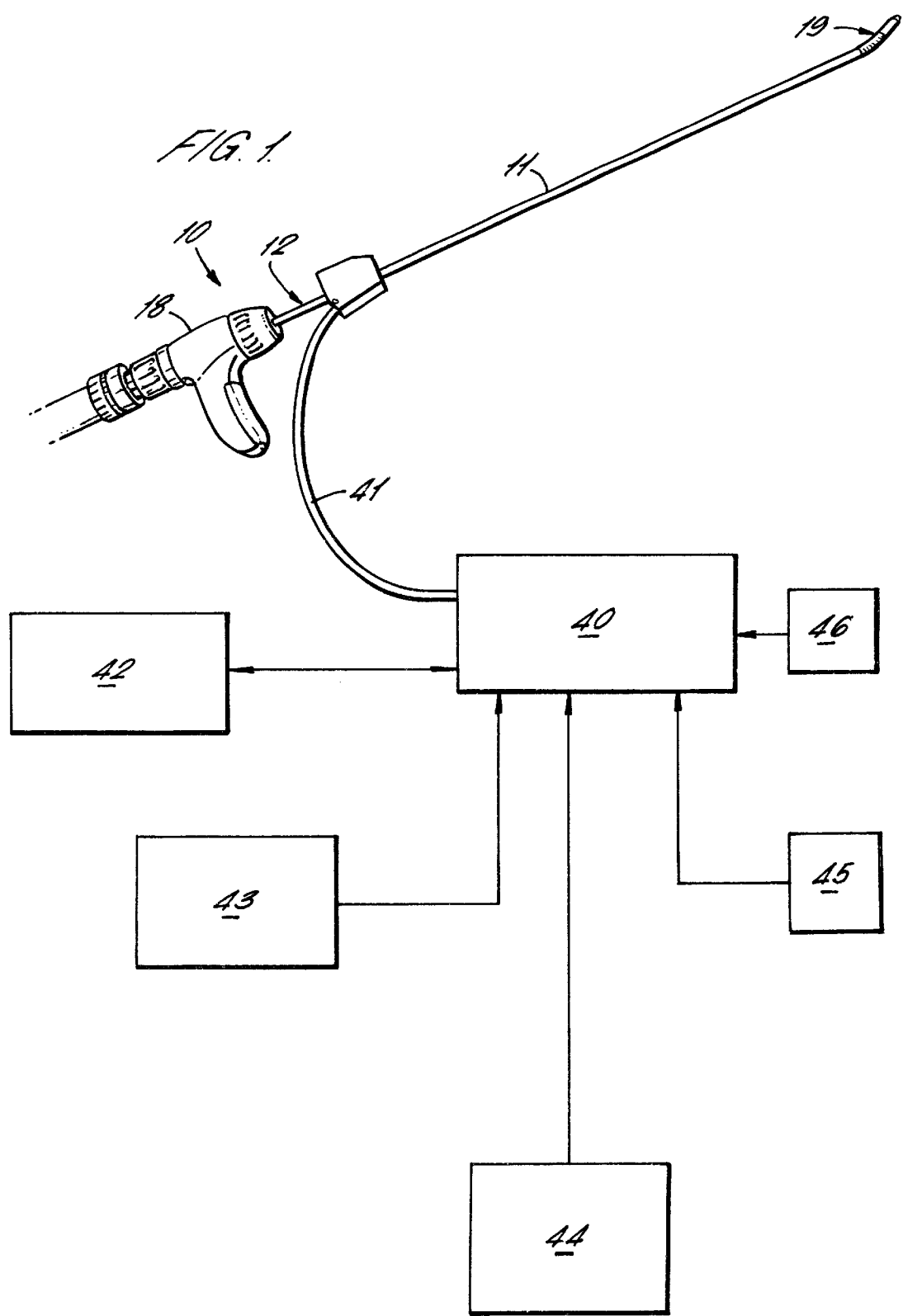
FIG. 1 is a schematic diagram of apparatus in accordance with a first embodiment of the present invention.
Figure 2:
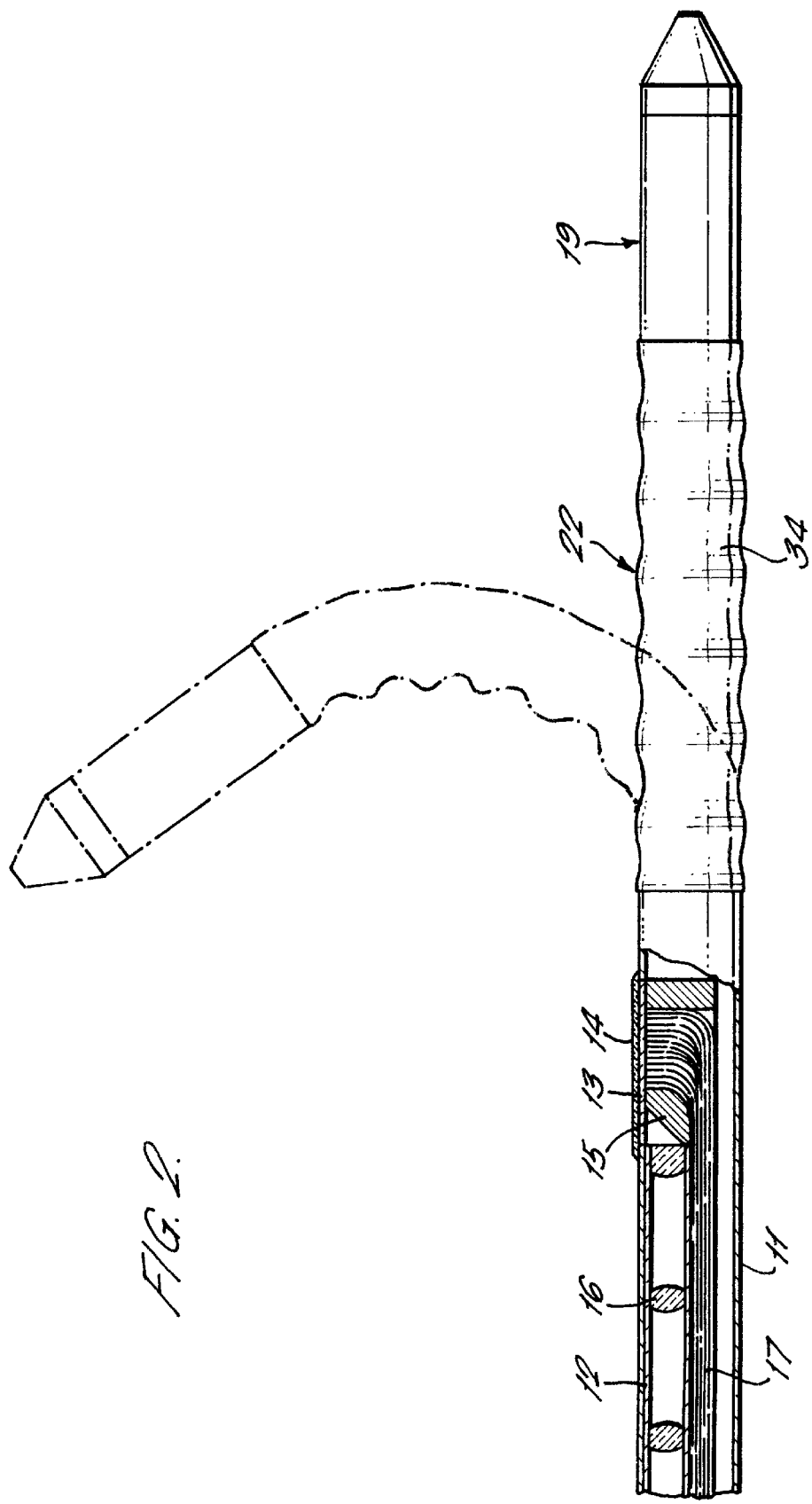
FIG. 2 is a cross-sectional view of the distal end of the insertion tube of FIG. 1.

With reference to FIGS. 1 and 2 which illustrate a preferred embodiment of the present invention, the apparatus 10 comprises an insertion tube 11 which in use can be inserted into a machine such as a gas turbine engine through an inspection port. The tube 11 is preferably manufactured from material such as steel.

Within the insertion tube 11, there is located a conventional side-viewing or orbital scanning optical scope 12. The insertion tube 11 provides a lateral viewing port 13 at the distal end which is preferably covered with a protective laser filter 14 to shield the components of the optical scope 12 from laser energy. A reflector 15 is associated with the viewing port 13 to reflect images of features positioned laterally of the insertion tube 11 into the optical train 16 of the scope 12. A light guide 17, eg. a bundle of optical fibres, is also provided through which light is transmitted to illuminate the field of view visible through the viewing port 13.

At it s proximal end the optical scope 12 is, in this example, connected to a housing 1a which includes an eye piece or camera attachment so that images transmitted through the scope 12 by the optical train 16 can be viewed either directly or, more preferably, displayed on a monitor in a known manner.

Alternatively, the scope 12 may incorporate an image to video converter such as a CCD chip (not shown) for transmitting an image to a monitor. As is well known in the art, such a device may be located either at the distal end of the scope 12, in which case the optical train 16 is unnecessary, or at the proximal end.

In the illustrated embodiment, the insertion tube 11 consists of a sheath tube into which a conventional orbital scanning borescope, eg. of the type described in GB 2280514, is removably fitted. Alternatively however, the optical scope 12 may be constructed as an integral part of the insertion tube 11. In this case the insertion tube 11 is connected directly to the housing 18.

Projecting from the distal end of the insertion tube 11 is a working head 19. As shown in FIGS. 3 and 4a, the head 19 consists of a barrel 20, a nozzle 21 at the distal end of the barrel 20 and a flexible coupling 22 connecting the proximal end of the barrel 20 to the distal end of the insertion tube 11.

An optical fibre 23 capable of transmitting laser energy, eg. a quartz fibre, extends through the length of the insertion tube 11 into the barrel 20.

Additionally, four pullwires 24 are connected to the barrel 20 and extend through the length of the insertion tube 11 to position control means described further below. The pullwires 24 are attached to the barrel 20 at equi-spaced peripheral locations. However, in the insertion tube 11 the pullwires 24 are preferably slidably contained within respective guide tubes (not shown) secured to one another and to one side of the insertion tube 11, spaced away from the components of the optical scope 12. In this way each pullwire 24 is able to slide axially unhindered within its respective guide tube.

This arrangement also ensures that the insertion tube 11 is not completely filled by the components of the optical scope 12, the laser fibre 23 and the pullwires 24, so that gas is able to flow from the proximal end of the insertion tube 11 to the distal end and into the head 19, the purpose of which is discussed further below. A dedicated gas supply tube may be provided within the insertion tube 11 for carrying gas therealong and to the head 19 or the whole available interior of the insertion tube 11 may simply be flooded with gas.

At the distal end of the insertion tube 11 an end fitting 35 is provided with suitably angled through-holes to receive and guide the optical fibre 23 and each of the pullwires 24 into the positions visible in FIG. 4, in which the optical fibre 23 is centrally located and the pullwires 24 are at equi-spaced peripheral locations. A gas flow passage through the end fitting 35 is also provided.

The proximal end of the barrel 20 defines a central passageway 25 for receiving the distal end of the optical fibre 23. One or more further passages 26 are also provided to allow gas flow communication between the interior of the insertion tube 11 and the interior of the barrel 20.

A lens 27 for focusing a laser beam transmitted through the optical fibre 23 is situated in the barrel 20 adjacent a shoulder 28. The lens 27 may be an aspheric lens, as shown, or a train of lenses (not shown) with or without as aspheric lens.

The nozzle 21 is secured to the distal end of the barrel 20, e.g. by cooperating threads, or in any convenient alternative manner. Preferably the nozzle 21 is secured so that it cannot become accidentally detached from the barrel 20 during use and hence lost within one working environment, such as a gas turbine engine. Nevertheless, the nozzle 21 may be releasably secured to the board 20 to allow different types of nozzle to be fitted if desired, e.g. if a welding filler material is to be used as discussed later with reference to FIGS. 6 and 7. The nozzle 21 may be made of copper, which has a high thermal conductivity, because this helps to prevent any spatter produced by a remedial operation such as welding from sticking to the nozzle 21. However, other materials such as ceramics could also be used. A spatter screen 29, e.g. of glass, may be located in the nozzle 21 to protect the lens 27 during use.

In an alternative embodiment (not shown), the optical fibre 23 extends all the way through the barrel 20 and out of the nozzle 21. In this way, a lens 27 and screen 29 are not necessary. The end of the optical fibre 23 will be shaped as appropriate to define the form of laser beam emitted from the fibre. For example, the fibre 23 may be shaped to emit a narrow focussed laser beam for concentrating laser power on a small area of the workpiece. Alternatively, the end of the fibre 23 may be shaped to produce a divergent beam which can be used, for example, to heat up an area of a workpiece.

Gas flow passages, indicated schematically by dotted lines in FIG. 3, are formed in the barrel 20 and nozzle 21 and/or in the periphery of the lens 27 and screen 29 to allow gas to flow through the head 19 and out of the nozzle 21.

The flexible coupling 22 consists of spring means, in particular two coil springs 30, 31. The first coil spring 30 is attached at one end to the insertion tube 11 and at the other end to a collar 32. The second spring 31 is also attached to the collar 32 at one end and to the barrel 20 at the other end. Four guide tubes 33 to receive and position the pull wires 24 are secured to the inner surface of the collar 32 at equi-spaced locations. A flexible sleeve 34 covers the coupling 22 and is secured in a gas-tight manner to the insertion tube 11 and the barrel 20.

The pullwires 24 are used to control movement of the head 19 relative to the insertion tube 11. Pulling on particular pullwires 24 causes the coil springs 30, 31 to compress and the head 19 to swing from side to side or up and down with respect to the longitudinal axis of the insertion tube 11. Pulling on all four wires retracts the two coil springs 30, 31 in order to bring the head 19 closer to the distal end of the insertion tube 11. Extending all four pullwires 24 allows the coil springs 30, 31 to extend and move the head 19 further away from the insertion tube 11. In this way, the head 19 can be steered so as to bring it round into the field of view of the optical scope 12, as shown by the chain lines in FIG. 2, and to move it towards and away from a desired workpiece in order to focus a laser beam on the workpiece as discussed below.

Figure 4B:
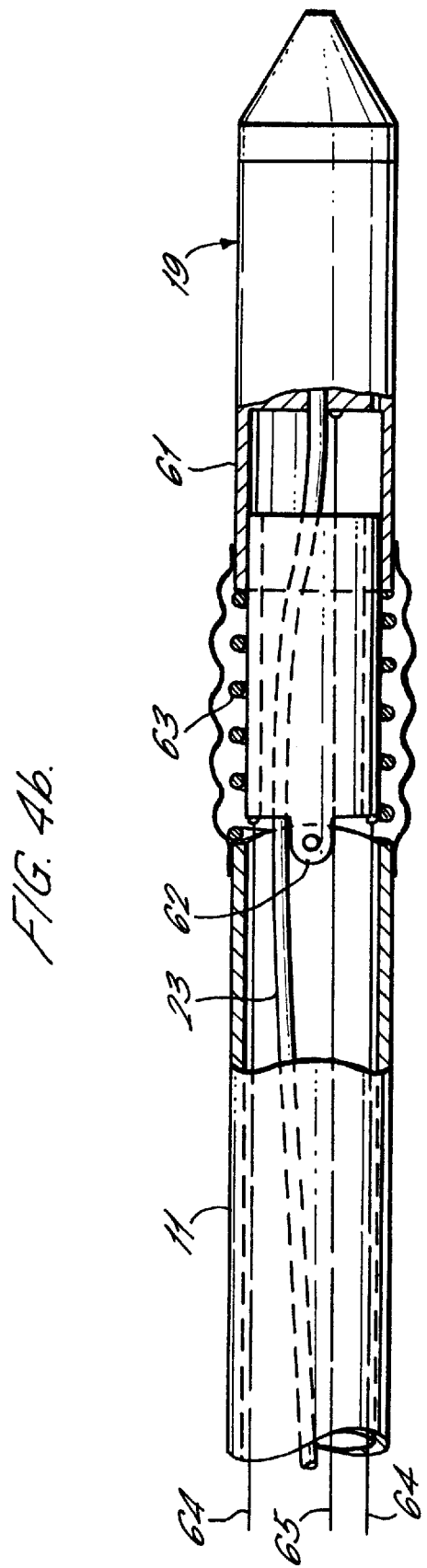
FIG. 4b is a side view, partly in cross-section, of an alternative flexible coupling.

It will be apparent to those skilled in the art that the springs 30, 31 and pull wires 24 are by no means the only possible configuration of flexible coupling 22. One example of an alternative flexible coupling is illustrated in FIG. 4b. In this case, a sleeve 60 projects in a proximal direction from the end of the barrel 20 and is slidably fitted over a cylinder 61 which is connected to the distal end of the insertion tube 11 by a pivot 62. Spring means, such as a coil spring 63 biases the barrel 20 away from the insertion tube 11.

Two pullwires 64 are attached to the cylinder 61 on either side of the pivot 62 in order to actuate the pivoting movement. Preferably, the end of the insertion tube 11 will be shaped with cutaways as shown in order to allow the cylinder 61 to pivot to an adequate angle. In this configuration, the cylinder 61 pivots only in one plane, for example up and down as shown in FIG. 4b. To allow pivoting in other directions, the insertion tube 11 must be rotated about its longitudinal axis in the same way as in a conventional orbital scan borescope.

A third pullwire 65 is attached to the barrel 20. The third pullwire 65 can be pulled back in order to oppose the action of the spring 63, causing the sleeve 60 to slide to a greater extent over the cylinder 61, in order to bring the barrel 20 closer to the distal end of the insertion tube 11. Relaxing the pullwire 65 allows the spring 63 to extend and move the barrel 20 further away from the insertion tube 11.

As before, this embodiment of flexible coupling is covered by a flexible sleeve 34 which is secured in a gas-tight manner to the barrel 20 and the insertion tube 11. It will also be apparent that in this configuration the optical fibre 23 may need to be guided around the pivot 62 by any appropriate means and then restored to a location coincident with the longitudinal axis of the device.

To allow the head 19 to bend to a greater angle relative to the tube 11, for example to bring it further into the field of view of the optical scope 12, it may be necessary to include two (or more) pivotally mounted cylinders 61a, 61b as shown in FIG. 4c, from which some of the pullwires have been omitted for the sake of clarity.

The extent to which the head 19 can be bent relative to the insertion tube 11 is limited by the bend radius of the optical fibre 23 as well as the configuration of the flexible coupling 22. However, even before the fibre 33 breaks, it will deform and allow some of the light transmitted through it to escape. If a high power laser is being transmitted then sufficient may escape to cause heating of the insertion tube 11 and its contents, which may be problematic. Therefore, the flexible coupling 22 should be designed and dimensioned to avoid approaching the maximum bend radius of the optical fibre 23 to prevent this problem.

The other components of the apparatus of the present invention are illustrated schematically in FIG. 1. These include a central control module 40 to which the insertion tube 11 is connected by flexible cable 41. The central control module 40 receives the other inputs to the system as described below.

A control computer 42, linked to the central control module 40, receives and records information from the control module 40 as to the position of the working head 19 as it is steered by the pullwires 24. In an automatic mode of the system, described further below, the control computer 42 also sends signals to the control module 40 to control movement of the head 1–9 and the supply of laser energy to the fibre 23.

A conventional light source 43 provides light which is transmitted by the light guide 17 through the cable 41 and the insertion tube for illuminating the field of view of the optical scope 12.

A laser source 44 generates a laser beam for transmission via the optical fibre 23 through the cable 41 and the insertion tube 11 to a workpiece. The source 44 may be a diode laser device or a YAG laser device, but any type may be used which is able to supply a laser of the desired power.

In one embodiment, the operation of which is described in more detail below, the laser source 44 is required to supply different types of laser for power visible laser beam which will provide a clearly visible spot of light on a workpiece, to be used for positioning purposes, without damaging the workpiece. The laser source 44 must also be able to provide a higher power laser beam which is used to carry out remedial operations such as drilling or welding on a workpiece. The power of the laser beam required to perform such operations and the length of time for which it must be applied will depend on the material of the workpiece and the type of operation to be carried out. Typically (but not exclusively), the higher power laser beam will not be visible and will be in the range of 10–180 W.

The laser spot size will also affect the power required to produce a melt zone of a given depth in a given material. By way of example only, the following table shows the power required for a spot size of 0.3 mm and 0.6 mm to produce various melt zone depths in stainless steel.

| MELT ZONE DEPTH FOR VARIOUS INPUT POWER LEVELS (STAINLESS STEEL) | | |
| --- | --- | --- |
| POWER | DEPTH (mm) | |
| (WATTS) | SPOT SIZE = 0.6 mm | SPOT SIZE = 0.3 mm |
| 200 | 0.6 | 1.0 |
| 150 | 0.5 | 0.9 |
| 120 | 0.45 | 0.8 |
| 100 | 0.4 | 0.75 |
| 80 | 0.35 | 0.5 |
| 60 | 0.3 | 0.45 |
| 50 | 0.25 | 0.35 |
| 30 | 0.125 | 0.15 |
| 20 | 0.1 | 0.1 |
| 8 | not measurable | not measurable |

A gas source 45 provides an assist gas under pressure which passes through the cable 41 to flood the interior of the insertion tube 11 and hence to exit the nozzle 21 when remedial work on a workpiece is being carried out. For example, when the higher power laser is being used for welding operations, an inert gas, such as argon or helium, to shield the working area can be provided in the same way as in conventional welding. Alternatively, if the higher power laser is performing a drilling operation or removing material from a workpiece in any way, oxygen can be provided to oxidise any material removed and prevent the formation of debris. En other situations, reactive gases or mixtures of different gases may be used, to suit the application.

Finally, a conventional power supply 46 is provided to power to entire system.

Inside the central control module 40, means are provided for adjusting the pullwires 24 in order to steer the working head 19. In this embodiment, the end of each pullwire 24 is wound around a rotatable cylinder 50. Rotation of the cylinder 50 winds in or unwinds wire, for shortening or lengthening the pullwire 24 and hence causing the coil springs 30, 31 in the flexible coupling 19 to retract or extend and to bend. Rotation of the cylinders 50 is provided by a servo amp 51 through suitable gearing 52 and is adjustable both manually, for example with a joystick control, and automatically by the control computer 42.

In a manual mode of operation, urging the joystick to the left or the right rotates the appropriate cylinders 50 in order to pull in the necessary pullwires 24 to cause the working head 19 to move to the left or right respectively. Similarly, urging the joystick up or down pulls the necessary pullwires 24 to cause corresponding movement of the head 19. In addition to movement in these two planes, the joystick control can be screwed in and out with respect to the central control module 40. Screwing the joystick outwardly actuates all four cylinders 50 to rotate simultaneously and to the same extent in order to cause the pullwires 24 to compress the coil springs 30, 31 and retract the working head 19. Conversely, screwing in the joystick towards the control module 40 rotates all four cylinders 50 simultaneously, letting out more wire and allowing the coil springs 30, 31 to extend the working head 19 further away from the distal end of the insertion tube 11.

FIG. 5 shows in schematic form how adjustment of the position of one of the four pullwires 24 is controlled.

A servo amp 51 drives the rotatable cylinder 50 through gearing 52, with a feedback loop provided in the usual way. The servo amp 51 receives inputs from the joystick control, if operated, and the control computer 42, if operated.

In the manual mode of operation the servo amp 51 will receive signals indicating when the joystick control is urged left, right, up or down and when it is being screwed in or out. In the case of the joystick being screwed in or out, signals are sent to the control systems for each other pullwire as well (as indicated by arrow A) so that all the pullwires are actuated simultaneously.

In the automatic mode of operation, the joystick is not operated and signals are supplied to the servo amp 51 by the computer 42, via a digital-to-analog converter.

In use, the insertion tube 11 is inserted into a machine such as a gas turbine engine through the normal inspection ports and is manipulated until a desired feature can be viewed through the optical scope 12. The image gathered by the optical scope 12 is delivered to a camera or image-to-video converter and displayed on a screen. The tube 11 is then clamped in a fixed position. A visible laser beam generated by the laser source 44 is transmitted through the optical fibre 23 into the barrel 20. The lens 27 focuses the divergent laser beam emitted from the laser fibre 23 into a narrow beam which exits the device through the nozzle 21. The pullwires 24 are adjusted using the manual control, i.e. the joystick, to steer the head 19 until the visible laser beam forms a spot of light resting on the feature of interest and to bring the spot into focus. The feature, e.g a crack, is then tracked by moving the laser spot along the feature by steering the head 19 with the pullwires 24. At each of a desired number of points along the feature the laser spot is stopped and focused, and data defining the position of the head 19 is recorded by the control computer 42 to form a record of the position of the crack or defect.

The apparatus is then converted to the automatic mode. The control computer 42 adjusts the control means to steer the head 19 so as to return the visible laser to the first point of the tracked feature. The control computer 42 may optionally request confirmation from an operator that the spot is in the appropriate position. Upon receiving the necessary confirmation (if requested), e.g. which is inputted via a computer keyboard, the more powerful working laser is generated instead and transmitted through the optical fibre 23. As before, this laser beam is focussed by the lens 27 and exits through the nozzle 21 to strike the target feature. The laser beam is applied to the feature for a predetermined length of time required to-perform a required remedial operation, e.g. drilling or welding etc. The power laser is then switched off and the visible laser switched on again and moved to the next tracked point on the feature by means of the control computer 42. Once again, the operator may be requested to confirm that the laser is in the appropriate position before the working laser is generated and applied to the feature for the appropriate length of time, and so on.

Whilst this process is being carried out, the gas supply 44 may provide an assist gas through cable 41 to the proximal end of the insertion tube 11. The gas flows along the length of the tube 11, through the barrel 20 and exits the nozzle 21 to flood the working area.

As those skilled in the art will appreciate, the above method is not the only way in which the apparatus of the invention may be used in order to perform an operation on a workpiece. For example, in the manual mode of operation an operator may find it difficult to manipulate the joystick so that the laser spot exactly tracks the defect and a different way of recording the position of the defect prior to the automatic mode of operation may be desired.

One option is to use the image of the workpiece displayed on the monitor. A cursor may be provided on the display, movable by a mouse or keyboard commands or the like, so that it can be positioned on the image of the defect. The operator positions the cursor at a number of points on the defect in turn and at each point enters a command, for example by clicking on the mouse or making a keyboard entry etc, to record the position of that point. The computer system employs suitable software to relate the image on screen and the cursor position to the actual position and size of the defect and thus to calculate the adjustments which will be necessary to the control means in order to steer the working head 19 to direct the working laser to the appropriate points.

When the apparatus is converted into automatic mode the processor adjusts the control means to drive the working head 19 so as to direct the laser beam to each point in turn for the appropriate length of time. As mentioned above, the operator may be asked for confirmation at each individual point or else the processor may calculate a path between the points and operate continuously.

In all cases, when the working laser is operating it may produce a great deal of light such that the image of the workpiece obtained by the optical scope 12 is obscured by the glare. It may therefore be desirable to filter the light received such that only infra-red is visible on the display, allowing the operator still to have some visual indication of what is happening. An appropriate filter may be included in the components of the optical scope in any convenient manner, in front of the camera or CCD, such that it can be brought into use when required.

As mentioned above, different types of remedial operation may be carried out on a workpiece by the apparatus of the present invention. Examples include drilling a hole at the base of the crack in order to prevent further crack propagation, ablation to smooth roughened areas and welding to knit together the sides of crack. In the latter case, it may not be possible to achieve a satisfactory weld unless additional filler material is supplied to fill the defect. Therefore, the present invention may also include means to supply a filler material to the workpiece.

In one embodiment, shown in FIG. 6, a conventional filler rod or wire 70 may be used, which is fed through the tube 11 and out of the head 19 through a port 71 in the side of the nozzle 21. The port 71 is preferably angled so as to direct the filler rod 70 to intersect the laser beam. Although FIG. 6 shows the same type of flexible coupling as FIG. 4b, the filler rod may be used in a device having any type of flexible coupling.

In an alternative embodiment. illustrated in FIG. 7, a filler powder may be used. In this case, a powder supply tube 72 is provided in the insertion tube 11 to feed powder to the head 19, for example, driven by the stream of assist gas. The nozzle 21 may be formed with an inner nozzle 73 through which the laser beam passes and an outer nozzle 74 through which filler powder is dispensed as shown. The powder may be delivered to the outer nozzle 74 through one or more ports 75 communicating with the powder supply tube 72.

In this way, a remedial operation can be accurately carried out in situ on a workpiece in an inaccessible location without physically contacting the workpiece. It will be appreciated by those skilled in the art that a number of modifications may be made to the configurations described above without departing from the scope of the invention.

What is claimed is:

1. Apparatus for performing an operation on a workpiece at an inaccessible location, comprising a tube having a proximal end and a distal end, the distal end being insertable in use into an inaccessible location; a head flexibly coupled to the distal end of the tube; control means operable to adjust the position of the head with respect to the tube; means to transmit laser energy through the tube to the head and out of the head; viewing means for gathering and displaying an image of the workpiece; tracking means operable to identify and record the position of one or more selected points on the workpiece; a processor operable to actuate the control means to move the head so as to direct laser energy to the selected point or, sequentially, to each of the selected points on the workpiece and to control the laser transmission means so as to perform the desired operation.

2. Apparatus as claimed in claim 1, wherein the tracking means comprising means to transmit a beam of visible light through the tube and out of the head, manual actuation means operable to move the head so as to direct the light beam to strike one or, sequentially, more than one desired point on the workpiece and wherein the processor is operable to record data representative of the position of the or each point.

3. Apparatus as claimed in claim 2, wherein the manual actuation means comprises a joystick.

4. Apparatus as claimed in claim 2, wherein the laser transmission means is adapted to selectively supply a lower power visible laser beam and a higher power laser beam for performing operations on the workpiece.

5. Apparatus as claimed in claim 1, wherein the tracking means comprises means to record the position of one or more selected points on the displayed image of the workpiece and wherein the processor is operable to relate the position of the or each point to the position of the head so as to actuate the control means to move the head to direct laser energy to the point, or, sequentially, to each point.

6. Apparatus as claimed in claim 1, wherein the viewing means comprises an optical scope integral with the tube.

7. Apparatus as claimed in claim 1, wherein the viewing means comprises an optical scope removably located in the tube.

8. Apparatus as claimed in claim 6, wherein the viewing means further comprises one of a camera and an image-to-video conversion device, and a display.

9. Apparatus as claimed in claim 6, wherein the viewing means is adapted for viewing laterally of the distal end of the tube.

10. Apparatus as claimed in claim 1, wherein the control means and flexible coupling are selectively operable to move the head relative to the tube in three dimensions.

11. Apparatus as claimed in claim 1, wherein the flexible coupling comprises spring means extending between the distal end of the tube and the head.

12. Apparatus as claimed in claim 1, wherein the flexible coupling comprises at least one cylinder mounted between the tube and the head for pivotal movement relative to the tube, a sleeve attached to the head and axially moveable relative to the cylinder and spring means urging the head axially away from the tube.

13. Apparatus as claimed in claim 11, wherein the control means comprises a plurality of pull elements secured to the head, and to the cylinder if present, and extending through the tube and means to retract and extend the pull elements.

14. Apparatus as claimed in claim 13, wherein the pull elements comprise wires.

15. Apparatus as claimed in claim 14, wherein the proximal end of each wire is wound around a rotatable cylinder.

16. Apparatus as claimed in claim 1, wherein the flexible coupling is encased in a flexible sleeve attached to the tube and to the head.

17. Apparatus as claimed in claim 16, wherein the flexible sleeve is attached to the head and to the tube in a gas tight manner.

18. Apparatus as claimed in claim 1, wherein the means to transmit laser energy comprises an optical fibre.

19. Apparatus as claimed in claim 18, wherein the optical fibre terminates in the head and the head further includes means to focus a laser beam emitted from the optical fibre.

20. Apparatus as claimed in claim 19, wherein the focusing means comprises a train of lenses.

21. Apparatus as claimed in claim 19 or claim 20, wherein the focusing means includes an aspheric lens.

22. Apparatus as claimed in claim 19, wherein a protective screen is provided in the head, distally of the focusing means.

23. Apparatus as claimed in claim 18, wherein the optical fibre extends out of the head.

24. Apparatus as claimed in claim 23, wherein the distal end of the optical fibre is shaped so as to emit a focussed laser beam from the optical fibre.

25. Apparatus as claimed in claim 23, wherein the distal end of the optical fibre is shaped so as to emit a divergent laser beam from the optical fibre.

26. Apparatus as claimed in claim 1, wherein a laser filter is provided to protect the viewing means from laser energy.

27. Apparatus as claimed in claim 1, wherein the viewing means includes a filter to pass infra-red radiation only for display.

28. Apparatus as claimed in claim 1, wherein the tube and head are adapted to allow gas flow therethrough.

29. Apparatus as claimed in claim 28, further comprising a gas supply for supplying pressurised gas or a mixture of gases to the tube and head.

30. Apparatus as claimed in claim 29, wherein the gas is, or the mixture of gases includes, an inert gas.

31. Apparatus as claimed in claim 29, wherein the gas is, or the mixture of gases includes, oxygen.

32. Apparatus as claimed in claim 1, further comprising means to feed filler material through the tube and to dispense the filler material from the head.

33. A method of performing an operation on a workpiece at an inaccessible location comprising the steps of:
    positioning the tube with its distal end in the vicinity of the workpiece; gathering an image of the workpiece with the viewing means and displaying the image; identifying and recording the position of one or more selected points on the workpiece; and operating a processor to move the head and to supply laser energy through the tube so as to direct the laser energy to the point or, sequentially, to each point so as to perform a desired operation.

34. A method as claimed in claim 33, wherein the identifying and recording step comprises transmitting a beam of visible light through the tube and out of the head; adjusting the position of the head with manual actuation means so as to direct the light beam to strike a selected point on the workpiece; recording the position of the point and, optionally, repeating the process on one or more further points.

35. A method as claimed in claim 33, wherein the identifying and recording step comprises viewing an image of the workpiece on a display; marking the position of a point on the workpiece on the display; recording the position of the point and, optionally, repeating the process on one or more further points.

* * * * *